US010376321B2

(12) United States Patent
DiMaio et al.

(10) Patent No.: US 10,376,321 B2
(45) Date of Patent: Aug. 13, 2019

(54) SHAPE SENSOR SYSTEMS FOR LOCALIZING MOVABLE TARGETS

(71) Applicant: Intuitive Surgical Operations Inc., Sunnyvale, CA (US)

(72) Inventors: Simon P. DiMaio, Sunnyvale, CA (US); Vincent Duindam, Mountain View, CA (US); David Q. Larkin, Menlo Park, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 597 days.

(21) Appl. No.: 14/916,854

(22) PCT Filed: Sep. 11, 2014

(86) PCT No.: PCT/US2014/055137
§ 371 (c)(1),
(2) Date: Mar. 4, 2016

(87) PCT Pub. No.: WO2015/038740
PCT Pub. Date: Mar. 19, 2015

(65) Prior Publication Data
US 2016/0206384 A1 Jul. 21, 2016

Related U.S. Application Data

(60) Provisional application No. 61/876,992, filed on Sep. 12, 2013.

(51) Int. Cl.
*A61B 34/20* (2016.01)
*A61B 17/32* (2006.01)
(Continued)

(52) U.S. Cl.
CPC ............ *A61B 34/20* (2016.02); *A61B 5/0538* (2013.01); *A61B 10/04* (2013.01);
(Continued)

(58) Field of Classification Search
CPC ..... A61B 10/04; A61B 17/16; A61B 17/1703; A61B 17/320016; A61B 2017/081;
(Continued)

(56) References Cited

U.S. PATENT DOCUMENTS 6,127,672 A  10/2000  Danisch
6,389,187 B1  5/2002  Greenaway et al.
(Continued)

FOREIGN PATENT DOCUMENTS

CN  200970224 Y  11/2007
CN  101099657 A  1/2008
(Continued)

OTHER PUBLICATIONS

International Preliminary Report on Patentability for Application No. PCT/US14/55137, dated Mar. 24, 2016, 9 pages.
(Continued)

*Primary Examiner* — Michael T Rozanski
(74) *Attorney, Agent, or Firm* — Haynes and Boone, LLP

(57) ABSTRACT

A method comprises receiving first shape data from a first elongated optical fiber section in a first shape sensor. The first elongated optical fiber section extends between a reference fixture and a first anatomic fixture coupled to a patient anatomy. The method further comprises determining a pose of the first anatomic fixture from the first shape data and tracking a pose change for the first anatomic fixture.

20 Claims, 12 Drawing Sheets

(51) Int. Cl.
    *A61B 5/053*     (2006.01)
    *A61B 17/17*     (2006.01)
    *A61B 46/00*     (2016.01)
    *A61B 10/04*     (2006.01)
    *A61B 17/16*     (2006.01)
    *A61B 34/30*     (2016.01)
    *A61B 90/00*     (2016.01)
    *A61B 17/08*     (2006.01)
    *A61B 18/00*     (2006.01)

(52) U.S. Cl.
CPC .. *A61B 17/1703* (2013.01); *A61B 17/320016* (2013.01); *A61B 46/00* (2016.02); *A61B 17/16* (2013.01); *A61B 34/30* (2016.02); *A61B 2017/081* (2013.01); *A61B 2018/00577* (2013.01); *A61B 2034/2061* (2016.02); *A61B 2090/0803* (2016.02); *A61B 2562/0266* (2013.01)

(58) Field of Classification Search
CPC .. A61B 2018/00577; A61B 2034/2061; A61B 2090/0803; A61B 2562/0266; A61B 34/20; A61B 34/30; A61B 46/00; A61B 5/0538
See application file for complete search history.

(56) References Cited

U.S. PATENT DOCUMENTS

| | | |
|---|---|---|
| 6,757,582 B2 | 6/2004 | Brisson et al. |
| 7,772,541 B2 | 8/2010 | Froggatt et al. |
| 7,781,724 B2 | 8/2010 | Childers et al. |
| 7,930,065 B2 | 4/2011 | Larkin et al. |
| 8,375,808 B2 | 2/2013 | Blumenkranz et al. |
| 8,488,130 B2 | 7/2013 | Duindam et al. |
| 8,900,131 B2 | 12/2014 | Chopra et al. |
| 8,945,095 B2 | 2/2015 | Blumenkranz et al. |
| 2006/0013523 A1 | 1/2006 | Childlers et al. |
| 2007/0032723 A1 | 2/2007 | Glossop et al. |
| 2009/0314925 A1 | 12/2009 | Van Vorhis et al. |
| 2009/0324161 A1 | 12/2009 | Prisco |
| 2011/0118749 A1 | 5/2011 | Prisco et al. |
| 2011/0202069 A1 | 8/2011 | Prisco et al. |
| 2011/0218546 A1 | 9/2011 | De La Fuente Klein et al. |
| 2016/0157939 A1 | 6/2016 | Larkin et al. |

FOREIGN PATENT DOCUMENTS

| | | |
|---|---|---|
| CN | 105473097 A | 4/2016 |
| JP | 2015504324 A | 2/2015 |
| WO | WO-2011100124 A1 | 8/2011 |
| WO | WO-2012168836 A2 | 12/2012 |
| WO | WO-2012168855 A1 | 12/2012 |
| WO | WO-2013057703 A1 | 4/2013 |
| WO | WO-2013061212 A1 | 5/2013 |
| WO | WO-2015017270 A1 | 2/2015 |

OTHER PUBLICATIONS

International Search Report and Written Opinion for Application No. PCT/US14/55137, dated Dec. 18, 2014, 13 pages.
Vertut, Jean and Phillipe Coiffet, Robot Technology: Teleoperation and Robotics Evolution and Deployment, English translation, Prentice-Hall, Inc., Inglewood Cliffs, NJ, USA 1986, vol. 3A, 332 pages.
Extended European Search Report for Application No. EP14844589.3, dated Mar. 20, 2017, 9 pages.
Office Action dated Jun. 22, 2018 for Chinese Application No. 201480050066 filed Sep. 11, 2014, 20 pages.

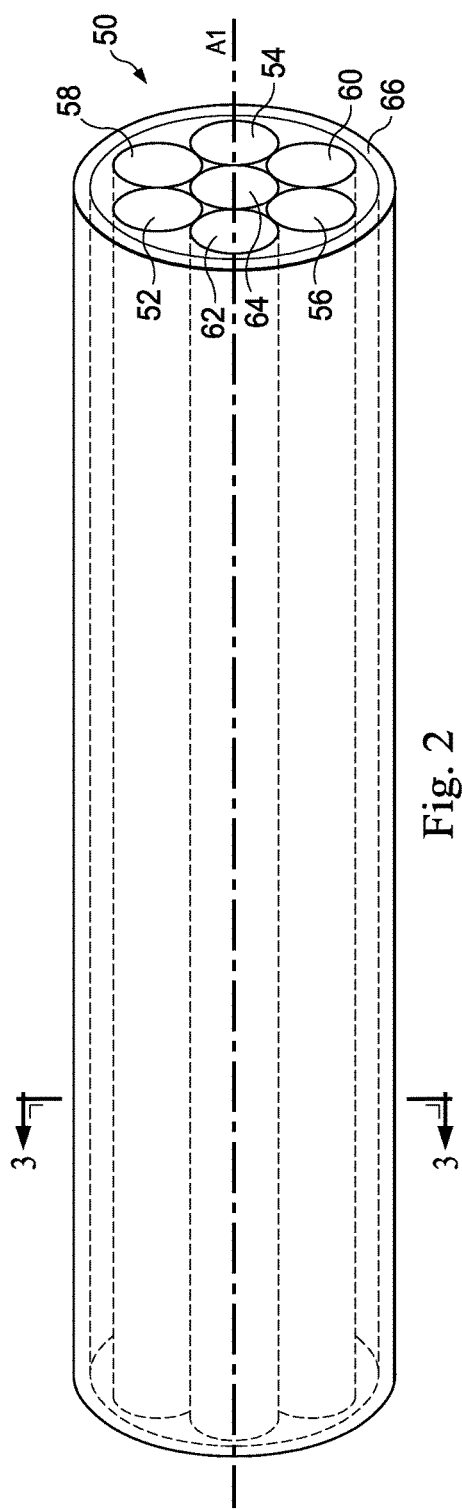
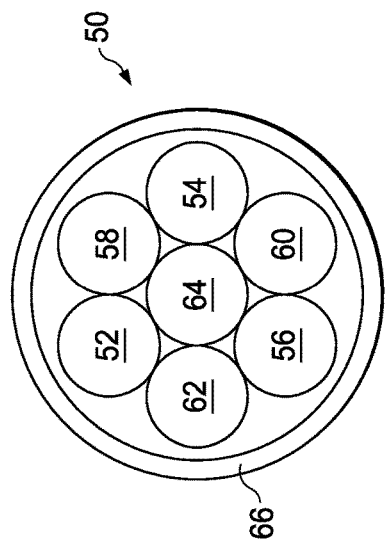

SHAPE SENSOR SYSTEMS FOR LOCALIZING MOVABLE TARGETS

CROSS-REFERENCE TO RELATED APPLICATIONS

This application claims the benefit of International Patent Application No. PCT/US2014/055137, filed Sep. 11, 2014, which claims priority from U.S. Patent Application No. 61/876,992 filed Sep. 12, 2013, which are all incorporated by the reference herein in their entireties.

FIELD

The present disclosure is directed to systems and methods for using shape sensor systems to track anatomical targets and/or interventional instruments, and more particularly to systems and methods using redundant shape sensors to improve the accuracy of shape sensor systems.

BACKGROUND

Minimally invasive medical techniques are intended to reduce the amount of tissue that is damaged during interventional procedures, thereby reducing patient recovery time, discomfort, and deleterious side effects. To track the location of anatomical targets, implanted devices, and/or interventional instruments (including surgical, diagnostic, therapeutic, or biopsy instruments) within a patient anatomy, minimally invasive sensor systems may be used. In existing systems, electro-magnetic (EM) navigation may be used to track the movement of interventional instruments, implanted devices, or targets in a patient anatomy. Although EM navigation systems are useful for many procedures, they may be subject to magnetic interference from other equipment in the surgical suite. For example, a C-arm of a fluoroscopic imaging system or metal instruments may generate magnetic interference with EM navigation systems, causing unacceptable errors in the tracking of an interventional instrument. In other existing systems, optical fiber shape sensor systems may be used to track the movement of interventional instruments in a patient anatomy. Optical fiber shape sensor systems monitor the strain at various points along a single optical fiber to determine the shape of the optical fiber. From the shape of the single optical fiber, the pose (position and orientation) of the various points along the optical fiber can be derived. The error associated with the derived poses for the various points along the single optical fiber may increase with distance from the optical fiber interrogator due to error accumulation. Improved navigation systems and methods are needed for tracking interventional instruments, implanted devices, and anatomic targets in surgical environments.

SUMMARY

The embodiments of the invention are summarized by the claims that follow the description.

In one embodiment, a method comprises receiving first shape data from a first elongated optical fiber section in a first shape sensor. The first elongated optical fiber section extends between a reference fixture and a first anatomic fixture coupled to a patient anatomy. The method further comprises determining a pose of the first anatomic fixture from the first shape data and tracking a pose change for the first anatomic fixture.

In another embodiment, a system comprises a bone fixation device, a shape sensor reference fixture, and an optical fiber shape sensor device coupled between the shape sensor reference fixture and the bone fixation device. The optical fiber shape sensor is configured to provide first shape data for determining a pose of the bone fixation device.

In another embodiment, a system comprises a bone fixation device, a shape sensor reference fixture, and a shape sensor device coupled between the shape sensor reference fixture and the bone fixation device. The shape sensor is configured to provide first shape data for determining a pose of the bone fixation device. The shape sensor device includes a plurality of optical fibers coupled to an elongated ribbon material to maintain the plurality of optical fibers in a predetermined spatial relationship.

In another embodiment, a system comprise a bone fixation device, a shape sensor reference fixture, and an optical fiber shape sensor device coupled at a proximal end to the shape sensor reference fixture and detachably coupled at the distal end to the bone fixation device. The optical fiber shape sensor is configured to provide first shape data for determining a pose of the bone fixation device. The system further comprises a coupling for detachably coupling the distal end of the bone fixation device to the optical fiber shape sensor device.

In another embodiment, a method comprises receiving first shape data from a first elongated optical fiber section in a first shape sensor. The first elongated optical fiber section extends between a reference fixture and an instrument fixture coupled to a medical instrument. The method also comprises determining a pose of the instrument fixture from the first shape data and tracking a pose change for the instrument fixture.

Additional aspects, features, and advantages of the present disclosure will become apparent from the following detailed description.

BRIEF DESCRIPTIONS OF THE DRAWINGS

Aspects of the present disclosure are best understood from the following detailed description when read with the accompanying FIGS. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 2 is a multi-core optical fiber component of the sensor system of FIG. 1.

FIG. 3 is a cross-sectional view of the multi-core optical fiber component of FIG. 2.

DETAILED DESCRIPTION

Figure 1:
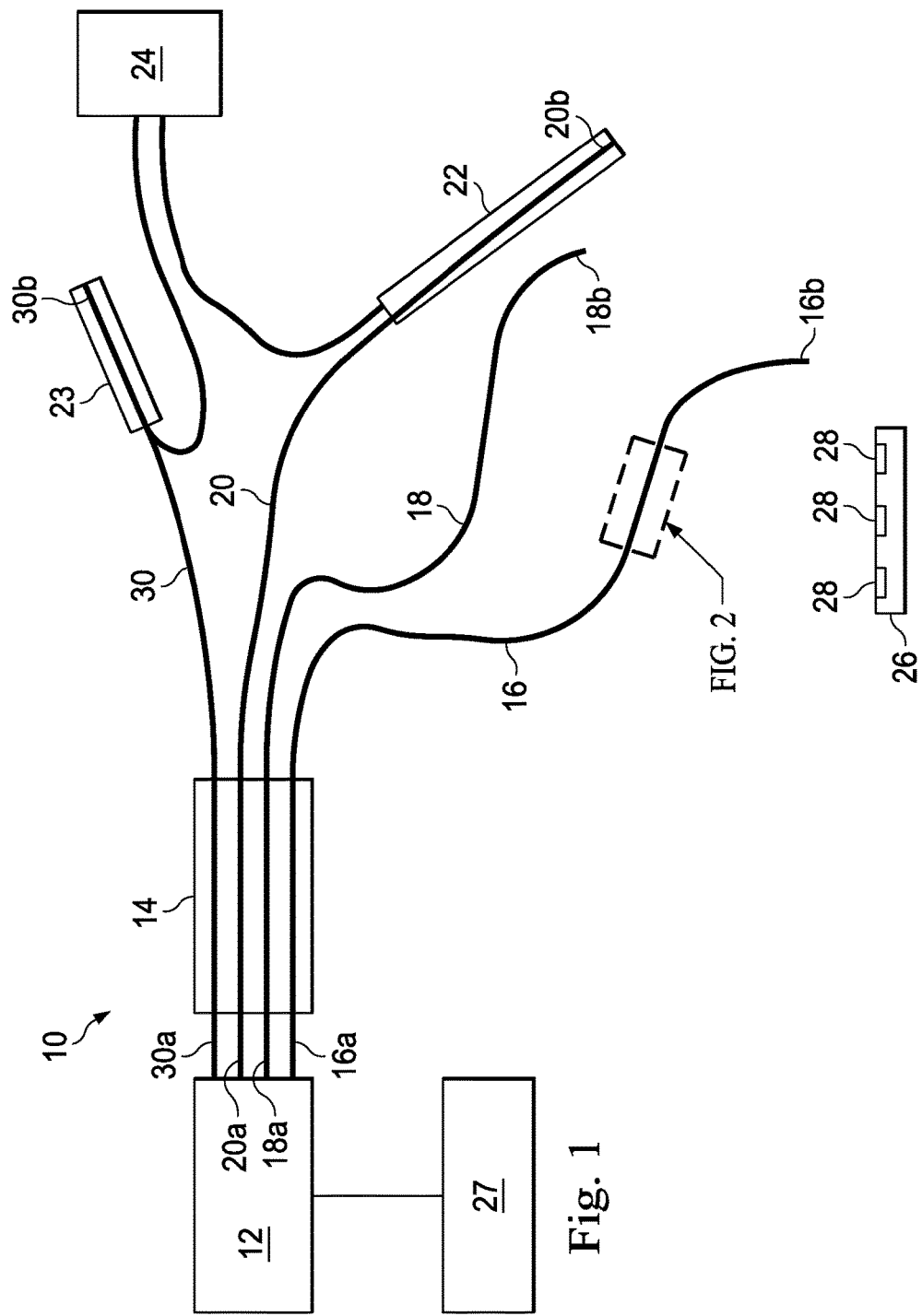
FIG. 1 is a sensor system in accordance with an embodiment of the present disclosure.

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

The embodiments below will describe various devices and portions of devices in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an elongated object. For the sake of illustration, the systems and methods described herein are generally described in terms of orthopedic surgery. However, the same systems and methods may be applied to procedures conducted on other areas of a patient anatomy.

Traditional optical navigation procedures for use in minimally invasive surgical procedures typically require a large camera head with a direct line of sight to anatomic reference fixtures and tool guide reference fixtures. Several disadvantages may be associated with traditional navigation approaches. For example, traditional optical tracking systems require a continuous line of sight between the camera and the tracked markers of the reference fixtures. Interruptions of the lines of sight can lead to workflow and safety issues. In arthroscopic surgery, for example, a small surgical field cluttered with instruments and an arthroscope may not permit line of sight optical tracking. Traditional optical tracking systems also employ reference fixtures that must be fixed to the patient by one or more bone screws. These reference fixtures may be bulky and limit surgical access. The methods and systems of this disclosure may be used as an alternative or supplement to traditional optical tracking methods and systems. Generally, the methods and systems of this disclosure involve the use of shape sensor systems to localize and track anatomical targets and instruments during an interventional procedure.

Referring to FIG. 1, a sensor system for use in, for example, surgical, diagnostic, therapeutic, biopsy, medical monitoring, or medical evaluation is generally indicated by the reference numeral 10. The sensor system 10 generally includes an interrogation system 12; a reference fixture 14; sensor devices 16, 18, 20, 30; an interventional instrument 22; a digitizing probe 23; a control system 24; a target fixture 26; and a sensor processing and control system 27. In various embodiments, one or more of these components of the sensor system may be omitted or multiple components of the same type may be included. As will be described in detail below, the sensor system 10 may include redundant sensor components which increase the accuracy of the shape sensing and pose determination functions of the system. The redundant sensor components may also identify the sources and locations of sensor inaccuracies, for example in regions with tight bends, high tensions, or significant twisting, and correct for those inaccuracies.

The interrogation system 12 generates light and detects returning light to determine the current shape of the sensor devices 16, 18, 20, 30. The interrogation system 12 may also process the returned data for display to the clinician. This information, in turn, in can be used to determine other related variables, such as pose, velocity and acceleration of the targets or instruments to which the sensor devices are connected. The sensor devices 16, 18 are coupled at proximal ends 16*a*, 18*a*, respectively, to the interrogation system 12. These proximal ends may be collocated or may be separated by known or measurable distance and orientation. Using the known transform, a common base frame can be used. The sensor devices 16, 18 also have distal ends 16*b*, 18*b*, respectively. The sensor device 20 is coupled at a proximal end 20*a* to the interrogation system 12 and at a distal end 20*b* to the interventional instrument 22. Although the sensor device 20 is shown extending entirely within or along the interventional instrument, in various alternative embodiments, the sensor device may extend only partially within or along the interventional instrument. The interventional instrument 22 is coupled to a control system 24 to receive, for example, power and communication signals. The sensor device 30 is coupled at a proximal end 30*a* to the interrogation system 12 and at a distal end 30*b* to the digitizing probe 23. Although the sensor device 30 is shown extending entirely within or along the probe 23, in various alternative embodiments, the sensor device may extend only partially within or along the probe. The digitizing probe 23 is coupled to the operated control system 24 to receive, for example, power and communication signals. The digitizing probe 23 may be used to identify and record navigational landmarks.

Each of the sensor devices 16, 18, 20, 30 is coupled to the reference fixture 14 at an intermediate portion along its length between the proximal and distal ends. The poses of the coupled portions of the sensor devices 16, 18, 20, 30 are held fixed by the reference fixture 14. Further, the poses of the coupled portions of the sensor devices 16, 18, 20, 30 are maintained in known kinematic relationships with respect to each other by the reference fixture 14. For example, the relationships between sensors and fixtures may be fixed, such as where the sensor device does not move with any degree of freedom relative to the reference fixture. Alternatively, the relationships between sensors and fixtures may be movable but known, such as where a sensor is movable relative to the reference fixture within a known range. For example, a reference fixture may have a rotating joint with a known rotation angle, but the relative position of the sensors to each other and to the reference fixture is still known. The reference fixture 14 may be, for example, formed of a rigid metal, polymer, or ceramic material and may include grooves, tubes, clamps, and/or other mechanical connectors that receive a portion of the sensor device and maintain it in a fixed relationship with respect to the fixture and with respect to the other coupled sensor devices. In one example, the reference fixture may be formed of an aluminum plate with several machined, tight-fitting parallel grooves to which the sensor devices may be glued or otherwise affixed. The position and orientation offsets between the coupled sensor devices are thus known at the location at which the sensor devices are coupled to the reference fixture 14. In various alternative embodiments, the reference fixture 14 may be located adjacent to the patient and imaged with the patient to provide a reference fiducial within the image.

In use, the target fixture 26 is anchored to an anatomical structure of a patient anatomy. The target fixture 26 includes connectors 28 for fixing a portion of one or more sensor devices 16, 18 to the target fixture and maintaining the fixed portions of the sensor devices in a predefined shape or pose. The sensor devices may be glued, mechanically held, or otherwise affixed within the target fixture. In one example, the target fixture may be a small aluminum plate with a plurality of tight-fitting grooves in which portions of the sensor devices are maintained in fixed kinematic relationships. Additional configurations for target fixtures with bone fixation devices are described in later embodiments.

The sensor devices 16, 18, 20, 30 may each include a single optical fiber having one or more optical cores. Alternatively, each sensor device may include multiple optical fibers, each with one or more optical cores. As shown in FIGS. 2 and 3, a single optical fiber 50 may have multiple optical cores, 52, 54, 56, 58, 60, 62, 64 within a cladding 66. In one embodiment, the multi-core optical fiber has a diameter of approximately 200 μm. In other embodiments, the dimensions may be larger or smaller. In alternative embodiments, the sensor device may have more or fewer than seven cores.

Each core in a single core or multi-core optical fiber may be single-mode with sufficient distance and cladding separating the cores such that the light in each core does not interact significantly with the light carried in other cores. Each core may include Fiber Bragg Gratings (FBGs) to provide strain measurements in one or more dimensions. Various systems and methods for monitoring the shape and relative position of an optical fiber in three dimensions are described in U.S. patent application Ser. No. 11/180,389, filed Jul. 13, 2005, disclosing "Fiber optic position and shape sensing device and method relating thereto;" U.S. Provisional Pat. App. No. 60/588,336, filed on Jul. 16, 2004, disclosing "Fiber-optic shape and relative position sensing;" and U.S. Pat. No. 6,389,187, filed on Jun. 17, 1998, disclosing "Optical Fibre Bend Sensor," which are incorporated by reference herein in their entireties. In other alternatives, sensors employing other strain sensing techniques such as Rayleigh scattering, Raman scattering, Brillouin scattering, and Fluorescence scattering may be suitable.

In some embodiments, an array of FBG's is provided within each core. Each FBG comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the FBG's, the modulations are spaced by a known distance, thereby causing reflection of a known band of wavelengths. However, when a strain is induced on the fiber core, the spacing of the modulations will change, depending on the amount of strain in the core. Alternatively, backscatter or other optical phenomena that vary with bending of the optical fiber can be used to determine strain within each core.

Thus, to measure strain, light is sent down the fiber core, and characteristics of the returning light are measured. In this embodiment, the interrogator 12 generates and receives the returned light for each core. In alternative embodiments, more than one interrogator may be used. The FBG's produce a reflected wavelength that is a function of the strain on the fiber and its temperature. This FBG technology is commercially available from a variety of sources, such as Smart Fibres Ltd. of Bracknell, England. Use of FBG technology in position sensors for robotic surgery is described in U.S. Pat. No. 7,930,065, filed Jul. 20, 2006, disclosing "Robotic Surgery System Including Position Sensors Using Fiber Bragg Gratings," which is incorporated by reference herein in its entirety.

When applied to a multicore fiber, bending of the optical fiber induces strain on the cores that can be measured by monitoring the wavelength shifts in each core. By having two or more cores disposed off-axis in the fiber, bending of the fiber induces different strains on each of the cores. These strains are a function of the local degree of bending of the fiber. For example, regions of the cores containing FBG's, if located at points where the fiber is bent, can thereby be used to determine the amount of bending at those points. These data, combined with the known spacings of the FBG regions, can be used to reconstruct the shape of the fiber. From the shape of the sensor device, a position and orientation of the distal ends 16b, 18b, 20b, 30b or other axial portions of the sensor devices may be determined.

Referring again to FIG. 1, the sensor processing and control system 27 includes at least one processor (not shown), and typically a plurality of processors, for processing the information received from the interrogation system 12. The system 27 includes programmed instructions to implement some or all of the methods described herein. While system 27 is shown as a single block in the simplified schematic of FIG. 1, the system may comprise a number of data processing circuits with a portion of the processing optionally being performed in different locations. Any of a wide variety of centralized or distributed data processing architectures may be employed. Similarly, the programmed instructions may be implemented as a number of separate programs or subroutines, or they may be integrated into a number of other aspects of the robotic systems described herein.

Figure 4:
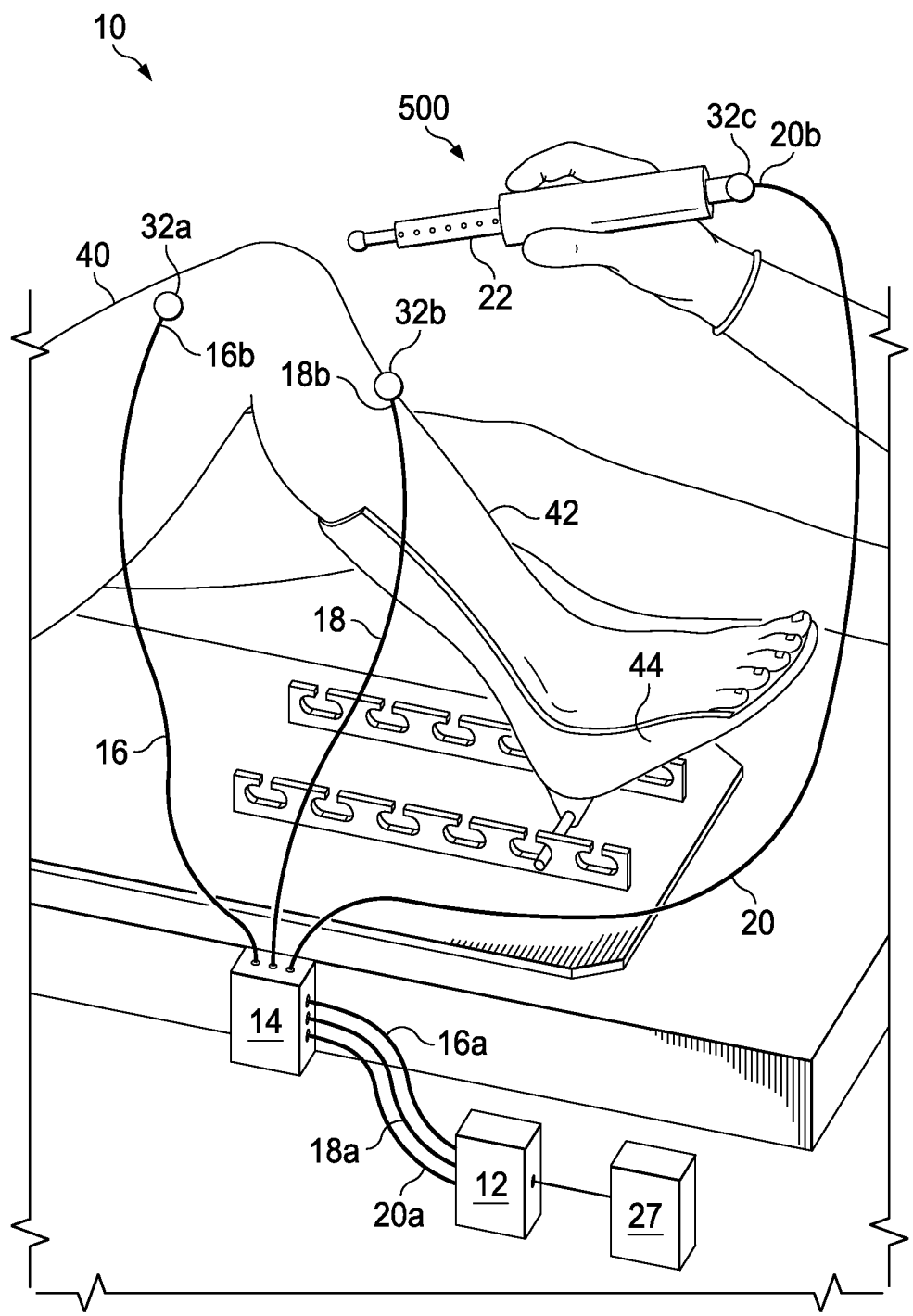
FIG. 4 is a sensor system with a plurality of optical fiber sensors in accordance with another embodiment of the present disclosure.

FIG. 4 illustrates a configuration 500 of the sensor system 10 in accordance with an embodiment of the present disclosure. In this embodiment, three sensor devices are attached to a common reference fixture and extend to different tools or anatomical locations. As will be described, the measured shapes of the sensor devices are used to determine the position and orientation of the distal ends of each sensor device. The relative location between the distal end of each sensor device can then be determined and tracked. For the sake of illustration, the systems and methods described herein are generally described in terms of orthopedic surgery on a patient leg. However, the same systems and methods may be applied to procedures conducted on other areas of a patient anatomy. In this configuration, the proximal ends 16a, 18a, 20a of sensor devices 16, 18, 20 respectively, are connected to the interrogation system 12. The sensor devices 16, 18, 20 are held by the reference fixture 14 in fixed or known kinematic poses. Position and orientation offsets between the sensor devices 16, 18, 20 at the reference fixture may be measured. The distal end 16b of the sensor device 16 is fixed to a target fixture 32a at a location on the patient femur 40. The distal end 18b of the sensor device 18 is fixed to a target fixture 32b at a location on the patient tibia 42. The distal end 20b of the sensor device 20 is coupled by a target fixture 32c to a handpiece of the instrument 22. The instrument 22 may be, for example, a bone preparation tool such as a burr, drill, saw, shaver, or other bone abrasion instrument. In other various embodiments, the instrument 22 may be, for example, a tissue cutting instrument; a tissue ablation instrument (e.g., using laser, radio-frequency (RF), microwave, plasma, or ultrasonic energy); a tissue approximation instrument, a tissue biopsy or sampling instrument, a tissue impedance measurement instrument, a tissue imaging instrument, or a therapeutic instrument. The target fixtures 32a, 32b, 32c hold the distal ends of the sensor devices 16, 18, 20, respectively, in fixed kinematic poses with respect to the target fixtures.

Figure 5:
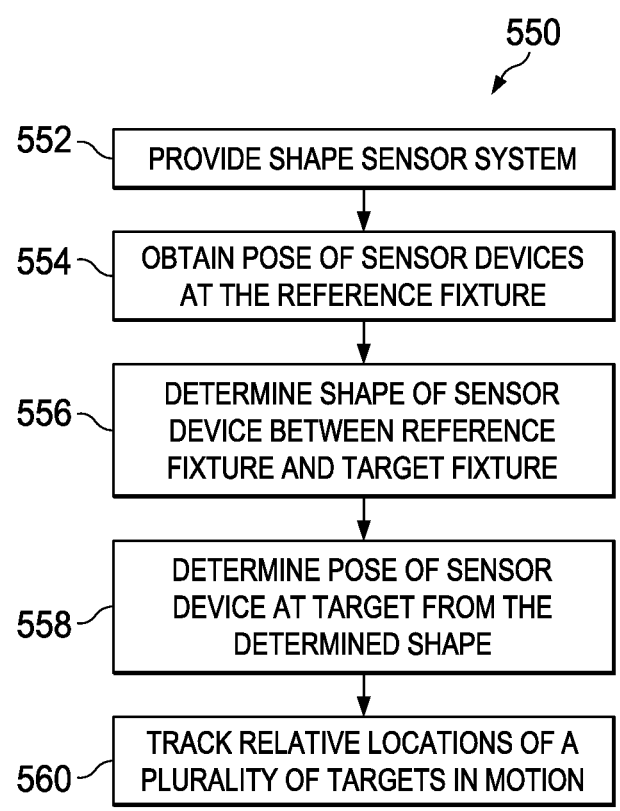
FIG. 5 illustrates a method of using the sensor system of FIG. 4.

FIG. 5 illustrates a method 550 for using the system 10 in the configuration 500 to track the relative locations of anatomical targets and instrument targets in motion. At 552, the system 10 in the configuration 500 is provided. At 554, the known or fixed pose of the sensor device 16 at the reference fixture 14 is obtained. At 556, the sensor device 16 is interrogated to determine the shape of the of the sensor device between the reference fixture 14 and the target fixture 32a. More specifically, the FBG strain measurements are used to determine local bend measurements which define a bend in the fiber at a particular location along the length of the fiber. The series of local bend measurements are integrated to determine the shape along the fiber. At 558, the pose of the sensor device 16 at the target fixture 32a (relative to the base frame 14) is obtained using the determined shape of the sensor device 16. For example, with the sensor device held in a fixed pose by the reference fixture 14, the composite shape of the sensor device may be cumulatively applied to the fixed pose at the reference fixture to determine the pose of the sensor device at the target fixture 32a. In greater detail, shape sensing proves an estimate of shape at discrete segments of the sensor device. Transformations due to all discrete shape estimates are integrated to obtain end-point pose:

$$^{base}T_{tip} = {}^{base}T_1 \cdot \prod_{i=1}^{n} {}^{i}T_{i+1} \cdot {}^{n}T_{tip}$$

Where $^{base}T_{tip}$ is a homogenous transformation between the base of the shape sensor (e.g., a coordinate frame fixed at the reference fixture 14) and the distal tip. $^{i}T_{i+1}$ is the local shape transform estimated by the sensor at length segment i. Further information about computing transformation matrices ($^{i}T_{i+1}$) is found in U.S. Pat. No. 7,720,322 filed Jun. 30, 2008 disclosing "Fiber Optic Shape Sensor," which is incorporated by reference herein in its entirety. A calibration process may additionally be performed to correct for a known offset between the reference fixture 14 and the proximal end 16a of the sensor device 16 at the interrogation system 12.

Thus, the pose of the sensor device 16 at the target fixture may be determined in the reference frame of the reference fixture 14. Using a similar technique, the pose of the sensor device 18 at the target fixture 32b and the pose of the sensor device 20 at the target fixture 32c are determined with reference to the reference fixture 14.

At 560, the relative locations of the target fixtures 32a, 32b, and 32c may be tracked as the target fixtures are moved relative to the reference fixture. For example during a procedure to treat the patient, the leg may be mounted in a movable carrier 44. As the carrier 44 is moved between various discrete or non-discrete positions, the femur 40 and the tibia 42 are moved. As the bones move, the attached target fixtures and sensor devices are also moved and the position of the target fixtures is tracked by the sensor devices 16, 18. As the instrument 22 is moved to treat the patient leg, the target fixture 32c is moved and tracked by the sensor device 20. Thus, the relative location of the instrument with respect to the target fixtures on the femur and tibia may be tracked.

Figure 6:
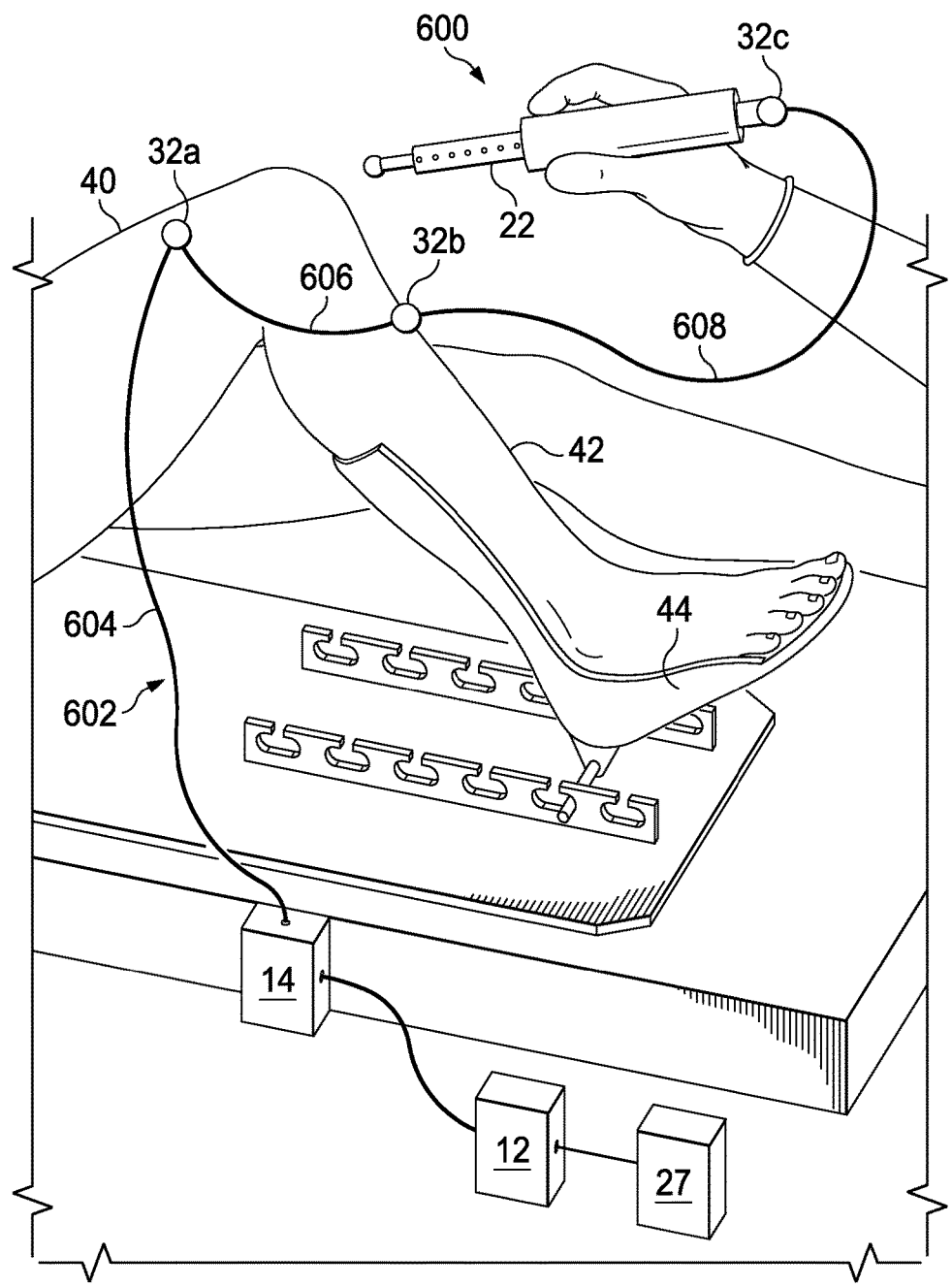
FIG. 6 is a sensor system with a sequentially linked optical fiber sensor in accordance with another embodiment of the present disclosure.

FIG. 6 illustrates a sensor system 600 in accordance with an embodiment of the present disclosure. In this embodiment, a sequentially linked shape sensor device may reduce any disruption to the surgical area caused by multiple independently movable shape sensor devices. In the configuration of the sensor system 600, a sensor device 602 includes segments 604, 606, 608. Segment 604 includes at least one optical fiber extending between the reference fixture 14 and the target fixture 32a fixed to the patient's femur. Segment 606 includes at least one separate optical fiber extending between the target fixture 32a and the target fixture 32b fixed to the patient's tibia. Segment 608 includes at least one separate optical fiber extending between the target fixture 32b and the target fixture 32c affixed to the handpiece of the surgical instrument 22. The distal endpoint of the fiber in segment 604 may be collocated with the proximal endpoint of the fiber in segment 606. Alternatively, the distal endpoint of the fiber in segment 604 may be separated from the proximal endpoint of the fiber in segment 606 by a known distance and orientation. For example, there may be a fixed known mechanical geometry between the endpoint or the locations of the endpoints may be tracked or measured relative to each other or to a reference frame. With a known relationship between the endpoints, transformations between the endpoints may be concatenated.

In one embodiment, miniature interrogators may be coupled to the target fixtures 32a and 32b. The main interrogator 12 may interrogate the shape sensor 604 to determine the pose of the target fixture 32a. The miniature interrogator at target fixture 32a may interrogate the shape sensor 606 to determine the shape of the sensor 606 and the pose of the target fixture 32b with reference to the target fixture 32a. Data about the shape of the segment 606 and the pose of the target fixture 32b may be conveyed through the segment 604 to the control system 27, for example, on a dedicated communication fiber or a selected core of a multi-core fiber or a selected core of a multi-core fiber, as an electrical signal, or wirelessly. The shape information about the segment 604 and 606 may be combined to determine a pose for the target fixture 32b relative to the reference fixture 14. The miniature interrogator at target fixture 32b may interrogate the shape sensor 608 to determine the shape of the sensor 608 and the pose of the target fixture 32c with reference to the target fixture 32b. Data about the shape of the segment 608 and the pose of the target fixture 32c may be conveyed through the segments 604, 606 to the control system 27, for example, on a dedicated communication fiber or a selected core of a multi-core fiber, as an electrical signal, or wirelessly. The shape information about the segment 604, 606, 608 may be combined to determine a pose for the target fixture 32c relative to the reference fixture 14. The pose of the fixture 32c is determined by computing transformations between the fixture 32c, the fixture 32b, the fixture 32a and the reference fixture 14. For example, after determining the shape of the sensor 608 and the pose of the fixture 32c in the reference frame of the fixture 32b, the pose of the fixture 32c is transformed (based on the shape of the sensor 606) into the reference frame of the fixture 32a. Then, the pose of the fixture 32c in the reference from of fixture 32a is transformed (based on the shape of the sensor 604) into the reference frame of the reference fixture 14.

Alternatively, each of the miniature interrogators at target fixtures 32a, 32b may be equipped with a wireless communication device to transmit shape data wirelessly to the control system 27. In still another alternative, the miniature interrogators may be omitted and segments of the shape sensor device 602 may be coupled by optical couplers that permit interrogation across the connection. As the patient leg is moved during the surgical procedure, the sensor system 600 tracks the relative position of the target fixtures 32a, 32b, 32c. The configuration of the sensor system 600 may reduce attenuation loss because there are overall fewer FBG's in the system as compared to embodiments in which longer, individual shape sensors (with gratings along substantially their entire lengths) extend between the reference fixture and the individual target fixtures, In various alternative embodiments, any segment of the optical fiber may also carry non-shape related data. For example, the optical fiber may also carry signals transmitting information about device status (e.g., powered on, powered off, idle); instrument or target identification information; and usage count (e.g. for the instrument, the sensor devices, and/or the target fixtures). The non-shape related data may, for example, be transmitted over a dedicated core of a multi-core optical fiber or may be multiplexed with shape related data for transmission via a common core. The optical fiber may also transmit strain information from segments of the optical fiber that are in receipt of external forces. For example, strain information from a flexure element on an instrument handpiece may be transmitted via the optical fiber and used to estimate a linear force or torque applied to the flexure element. Further information about the use of optical strain sensing to measure force or torque applied to an instrument by a user or applied by the instrument to patient tissue is found in U.S. patent application Ser. No. 11/537,241 filed Sep. 29, 2006 disclosing "Force and Torque Sensing For Surgical Instruments" and U.S. Pat. No. 8,375,808 filed Sep. 29, 2007 disclosing "Force Sensing for Surgical Instruments," which are incorporated by reference herein in their entirety.

In various alternative embodiments, sensor device and target fixtures may be disposable after a single use. In further alternative embodiments, the optical fiber of the sensor device may be incorporated into an existing power or communication cable for instruments such as burrs, drills, saws, or other powered or networked instruments.

Figure 7:
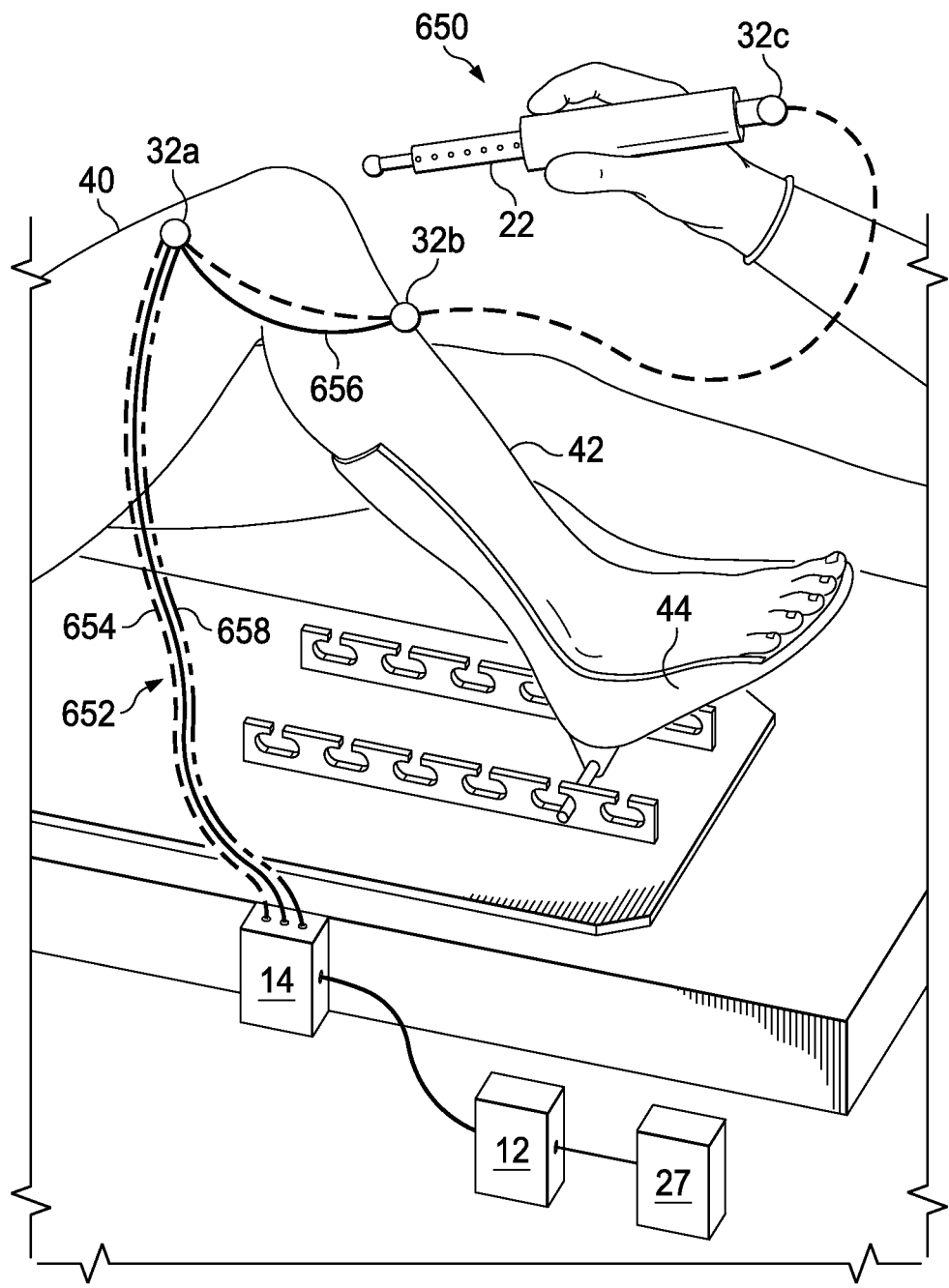
FIG. 7 is a sensor system with a plurality of optical fiber sensors in accordance with another embodiment of the present disclosure.

FIG. 7 illustrates a sensor system 650 in accordance with an embodiment of the present disclosure. In the configuration of the sensor system 650, a linked sensor device 652 includes staggered segments 654, 656, 658. Segment 654 includes at least one optical fiber extending between the reference fixture 14, the target fixture 32a, the target fixture 32b, and the target fixture 32c. Gratings may extend only along the portion of segment 654 between target fixtures 32b and 32c. When segment 654 is interrogated by the interrogator 12, only shape information about the portion of the segment 654 between fixtures 32b and 32c is returned. This limited use of FBGs may reduce attenuation loss compared to what would be expected if gratings extended along the entire length of the segment 654. Non-grated fiber experiences relatively low signal loss. Segment 656 includes at least one optical fiber extending between the reference fixture 14, the target fixture 32a, and the target fixture 32b. Gratings may extend only along the portion of segment 656 between target fixtures 32a and 32b. When segment 656 is interrogated by the interrogator 12, only shape information about the portion of the segment 656 between fixtures 32a and 32b is returned. Segment 658 includes at least one optical fiber extending between the reference fixture 14 and the target fixture 32a. Gratings may extend along the length of the segment 656 between the reference fixture 14 and the target fixture 32a. When segment 658 is interrogated by the interrogator 12, only shape information about the portion of the segment 658 between reference fixture 14 and target fixture 32a is returned. The shape information from segments 658 and 656 is combined with the shape information from segment 654 to determine the pose of the target fixture 32c. The shape information from segments 658 and 656 are combined to determine the pose of the target fixture 32b. The shape information from the segment 658 provides the pose information for the target fixture 32a. As the patient leg is moved during the surgical procedure, the sensor system 650 tracks the relative position of the target fixtures 32a, 32b, 32c.

Figure 8:
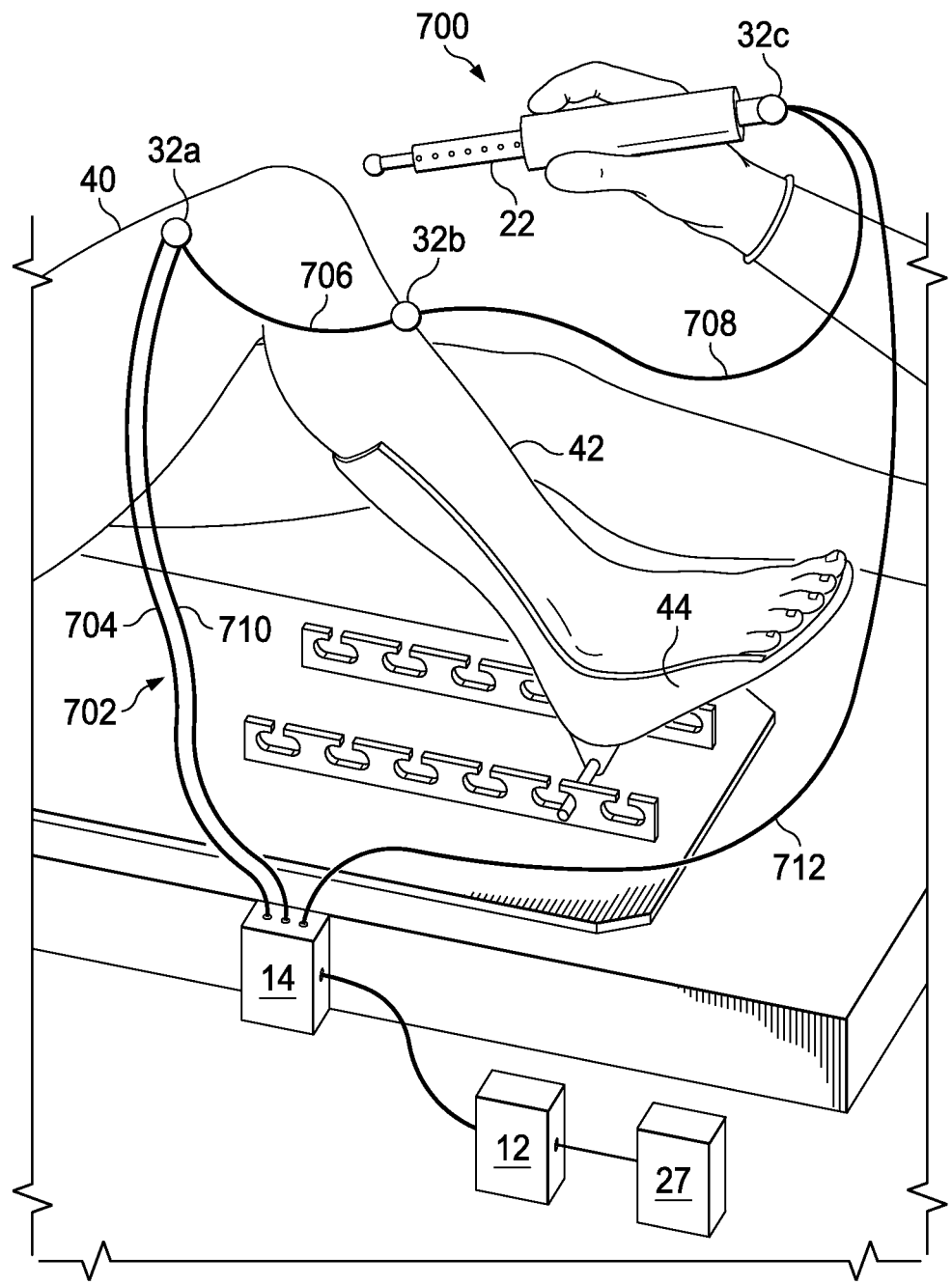
FIG. 8 is a closed loop sensor system in accordance with another embodiment of the present disclosure.

FIG. 8 illustrates a sensor system 700 in accordance with an embodiment of the present disclosure. In this closed-chain embodiment, redundant sensor devices are used with a linked shape sensor device 702 to reduce measurement error. In the configuration of the sensor system 700, a sensor device 702 includes segments 704, 706, 708. The shape of the segments 704, 706, 708 and the pose of the target fixtures 32a, 32b, 32c may be determined as described above for systems 600 and 650. In this embodiment, a sensor device 710 extends between the reference fixture 14 and the target fixture 32a. A sensor device 712 extends between the reference fixture 14 and the target fixture 32c. Using techniques as previously described, the sensor device 710 is interrogated to determine the sensor shape and the pose of the target fixture 32a. The determined pose of the target fixture 32a determined by the redundant sensor device 710 may be averaged or otherwise combined with the pose of the target fixture 32a determined by the sensor segment 704. Thus, the redundant sensor device 710 may be used to improve the accuracy of the determined pose of the target fixture 32a. The sensor device 712 is interrogated to determine the sensor shape and the pose of the target fixture 32c. The determined pose of the target fixture 32c determined by the redundant sensor device 712 may be averaged or otherwise combined with the pose of the target fixture 32c determined by the accumulation of sensor segments 704, 706, 708. Thus, the redundant sensor device 712 may be used to improve the accuracy of the determined pose of the target fixture 32c or to detect an error or breakage in the fiber. The redundant sensor device may also provide a check on the system operability since the closed chain should measure a transformation back to the reference fixture 14.

Figure 9:
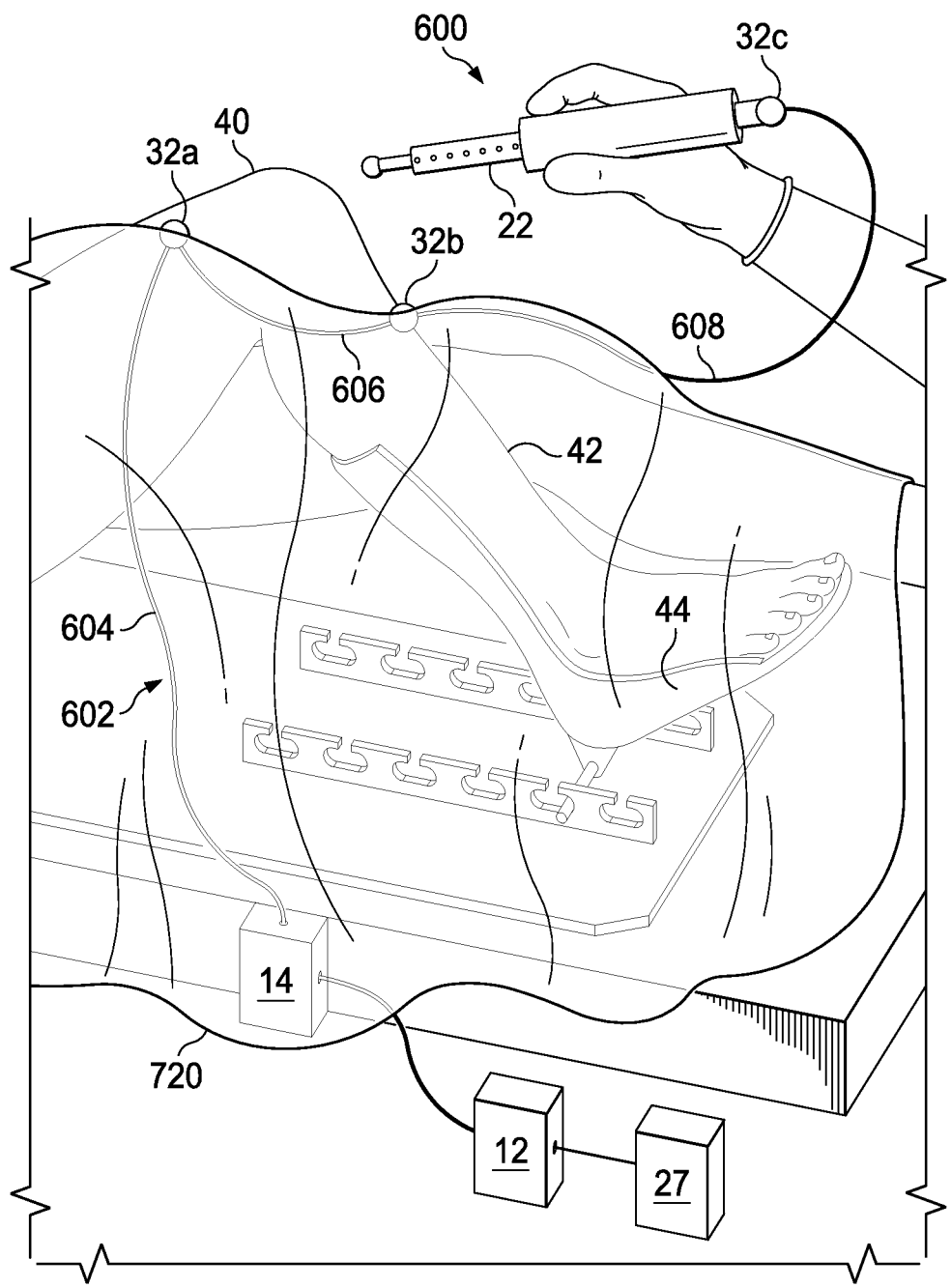
FIG. 9 is a sensor system incorporated into a sterile drape in accordance with another embodiment of the present disclosure.

Any of the above-described sensor systems may be integrated into a sterile drape to reduce any interference associated with independent sensor devices extending into the surgical area. FIG. 9 illustrates the sensor system 600 integrated into a sterile surgical drape 720. In this embodiment, the sensor segments 604, 606 are tethered, embedded, or otherwise attached to the surgical drape 720 along the length of the sensor segments so that the sensor segments move with the drape. The segment 608, extending to the instrument, may be partially attached to the surgical drape 720 or may be movable independently of the drape. The drape 720 may be adhered to the leg with adhesive material in the region of the target fixtures 32a, 32b. Alternatively, the drape 720 may held in place by directly connecting to the target fixtures 32a, 32b.

Figure 10:
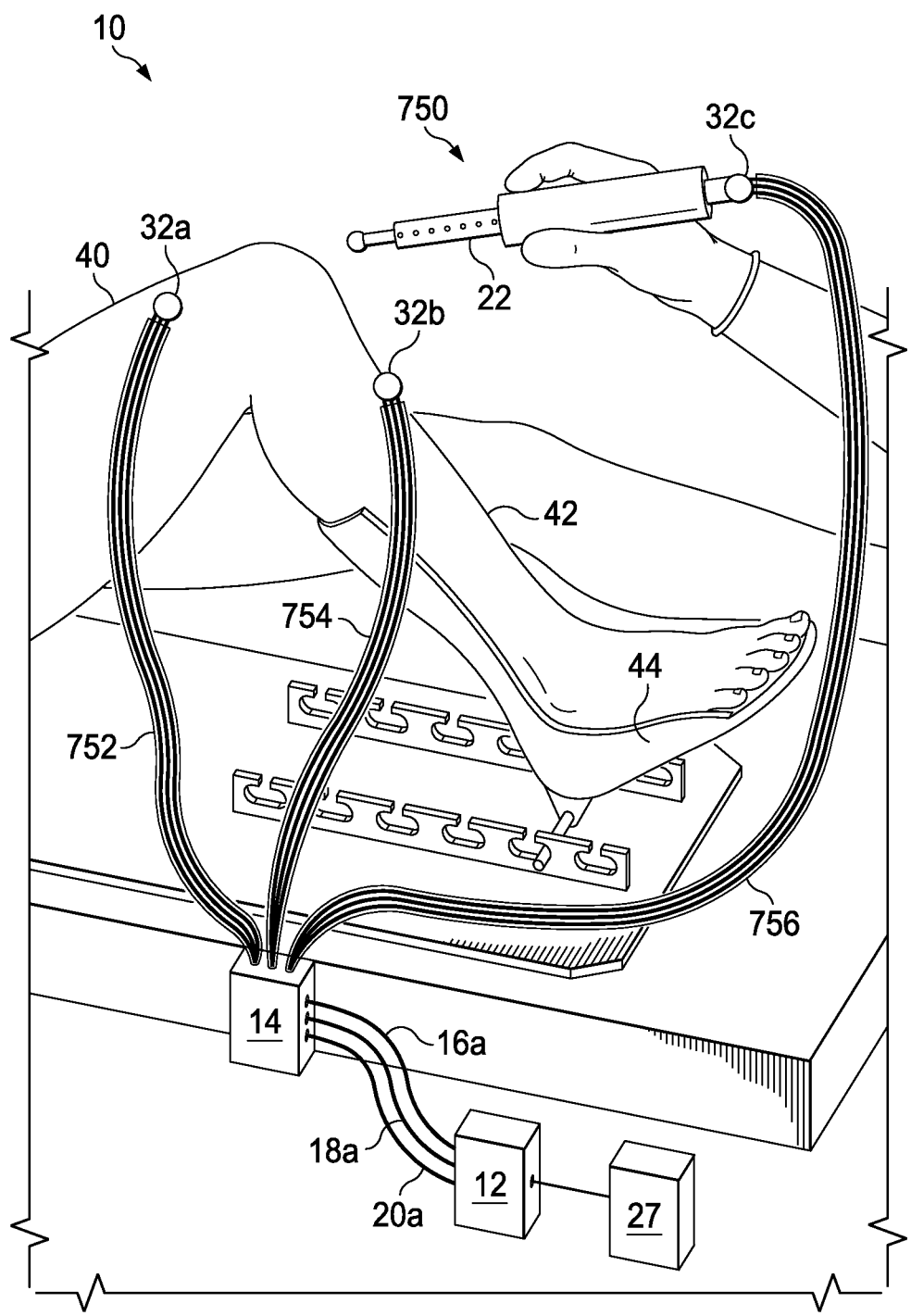
FIG. 10 is a sensor system with a plurality of redundant optical fiber sensors in accordance with another embodiment of the present disclosure.

FIG. 10 illustrates a sensor system 750 in accordance with an embodiment of the present disclosure. In this embodiment, three redundant sensor devices 752, 754, 756 are attached to the common reference fixture 14 and extend to different tools or anatomical locations. Each sensor device includes a plurality of (in this embodiment, three) optical fiber shape sensors. The optical fiber shape sensors may be single or multi-core. The sensor device 752 extends between the reference fixture 14 and the target fixture 32a. Each of the shape sensors of the sensor device 752 may be interrogated to determine a sensor shape and estimated pose for the target fixture 32a. The determined shapes and/or estimated poses for target fixture 32a may be averaged or otherwise combined to determine a refined estimate of the sensor device 752 shape and pose for the target fixture 32a. The sensor device 754 extends between the reference fixture 14 and the target fixture 32b and a similar method is used to determine a refined pose of the target fixture 32b. The sensor device 756 extends between the reference fixture 14 and the target fixture 32c and a similar method is used to determine a refined pose of the target fixture 32c. The optical fiber shape sensors that comprise the sensor devices of this embodiment may be assembled in a ribbon configuration with a known spatial relationship between the optical fibers. Generally, greater separation between the sensor devices in a ribbon configuration contributes to improved roll measurements and thus improved pose measurements.

Figure 11:
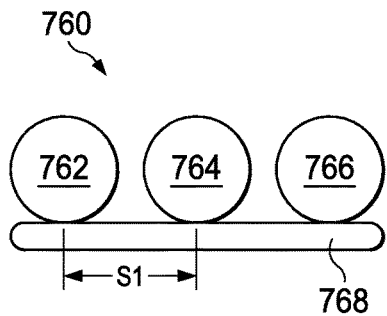
FIG. 11 illustrates a plurality of redundant optical fiber sensors in a ribbon configuration in accordance with another embodiment of the present disclosure.
Figure 12:
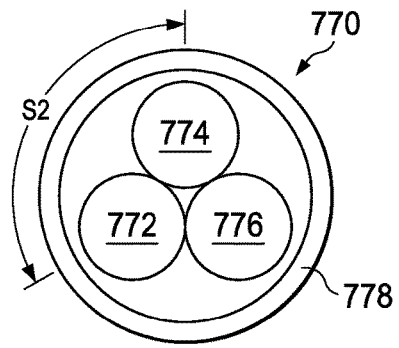
FIG. 12 illustrates a plurality of redundant optical fiber sensors in a ribbon configuration in accordance with another embodiment of the present disclosure.

FIG. 11 illustrates one embodiment of a ribbon configuration 760 including three optical fibers 762, 764, 766 that may be single- or multi-core fibers. The optical fibers 762, 764, 766 are affixed to a ribbon support material 768 which may be formed of a polymer, metal, natural fiber, or other flexible material including additional optical fibers. In this embodiment, the ribbon material may be elongated and generally flat. The optical fibers 762, 764, 766 are fixed to the ribbon material 768 with a constant linear spacing S1 maintain between the fibers. In various embodiments, the spacing may vary between different pairs of neighboring fibers, but the ribbon maintains the selected spacing between the neighboring fibers. The optical fibers 762, 764, 766 may be embedded in the ribbon or may be affixed to the ribbon material 768 by adhesives, mechanical couplings, or other known connective systems. FIG. 12 illustrates another embodiment of a ribbon configuration 770 including three optical fibers 772, 774, 776 affixed to a ribbon material 778 arranged in a tubular form. In this embodiment, the optical fibers are fixed to the inner surface of the ribbon material with a constant radial spacing S2 maintained between the fibers. In alternative embodiments, the optical fibers may be fixed to the outer surface of the ribbon material with constant spacing between the fibers.

Figure 13:
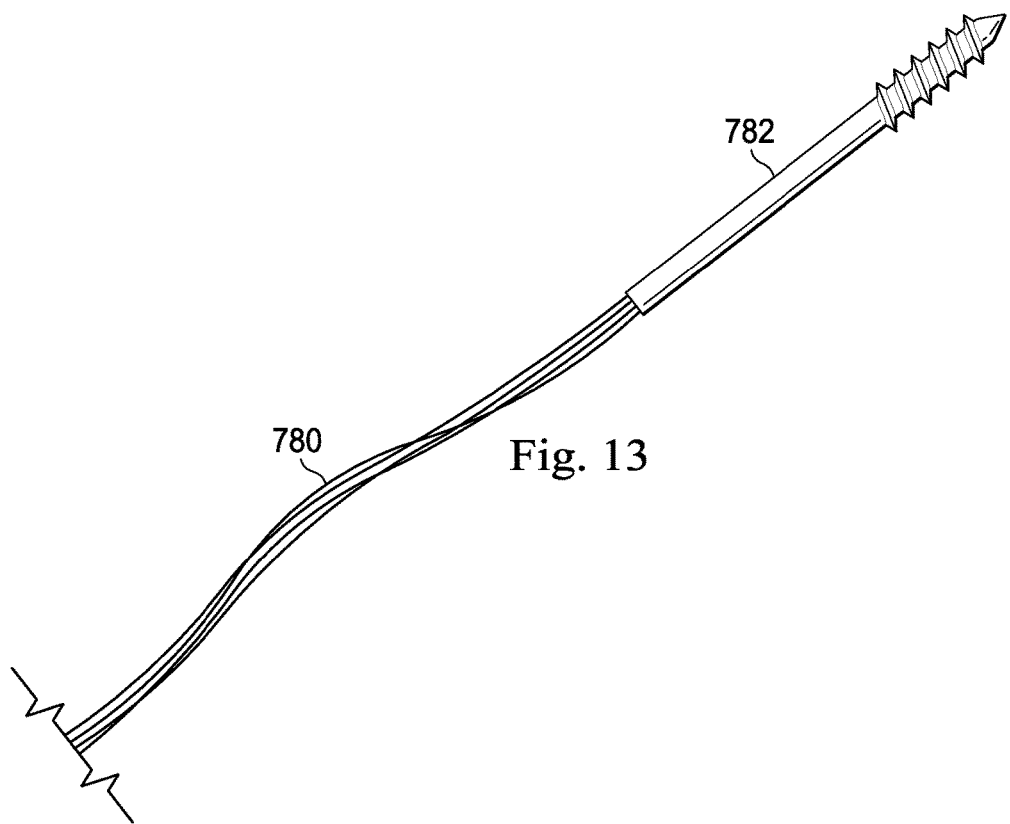
FIG. 13 illustrates an optical fiber sensor integrated into bone fixation hardware in accordance with another embodiment of the present disclosure

FIG. 13 illustrates an optical fiber sensor device 780 integrated into bone fixation hardware 782. The sensor device 780 may be substantially similar to any of the previously described sensor devices. In this embodiment, the bone fixation hardware is a bone screw, but in various alternative embodiments, the bone fixation hardware may be a bone clamp, bone plate, nail, pin, staple or other mechanical connector for coupling to bone. The bone fixation hardware 782 may be used as a target fixture in any of the previous embodiments. In this embodiment, the sensor device 780 is permanently coupled to the bone fixation hardware such that the sensor device may only be removed from the patient anatomy when the bone fixation hardware is removed.

Figure 14:
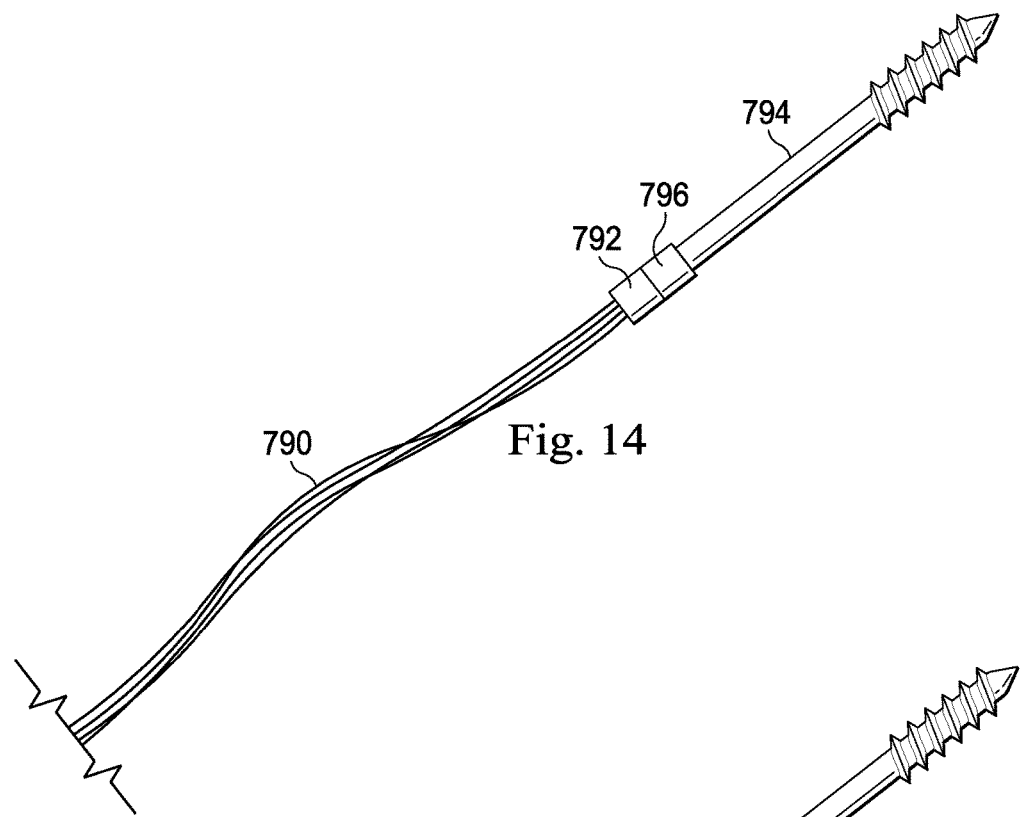
FIG. 14 illustrates an optical fiber sensor terminating at a coupling member for bone fixation hardware in accordance with another embodiment of the present disclosure.

FIG. 14 illustrates an optical fiber sensor device 790 attached to a coupling mechanism 792. Bone fixation hardware 794 is fitted with a coupling mechanism 796 that detachably connects to the coupling mechanism 792. When connected to each other, the coupling mechanisms 792, 796 maintain a distal end 791 of the sensor device 790 in a fixed pose relative to the bone fixation hardware 794. The coupling mechanisms 792, 796 may connect to each other with any known coupling system including a clip, a clamp, a twist lock, a threaded connection, a magnetic connection, or a snap-fit connection. The coupling mechanisms 792, 796 may be detachable to allow the bone fixation hardware to become disconnected from the sensor device 790. With the coupling mechanisms of this embodiment, a target fixture and a sensor device may be quickly connected and disconnected.

Figure 15:
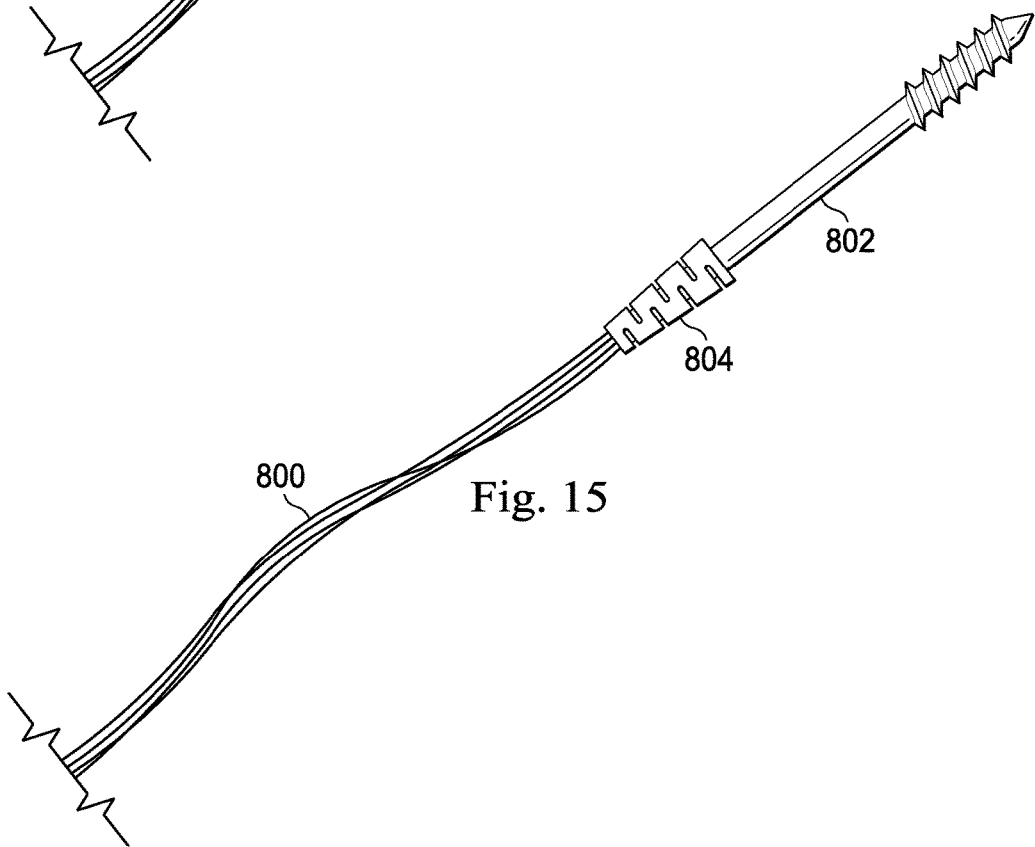
FIG. 15 illustrates an optical fiber sensor with strain relief at a coupling to bone fixation hardware in accordance with another embodiment of the present disclosure.

FIG. 15 illustrates an optical fiber sensor device 800 coupled to bone fixation hardware 802 with a strain relief device 804. The strain relief device 804 prevents tight fiber bends or other high strain configurations of the sensor device 800 at the connection to the bone fixation hardware 802. The strain relief device 804 may be a flexible plastic or rubber jacket with or without perforations, a coil, a loop, or other known flexible interconnection device.

Figure 16:
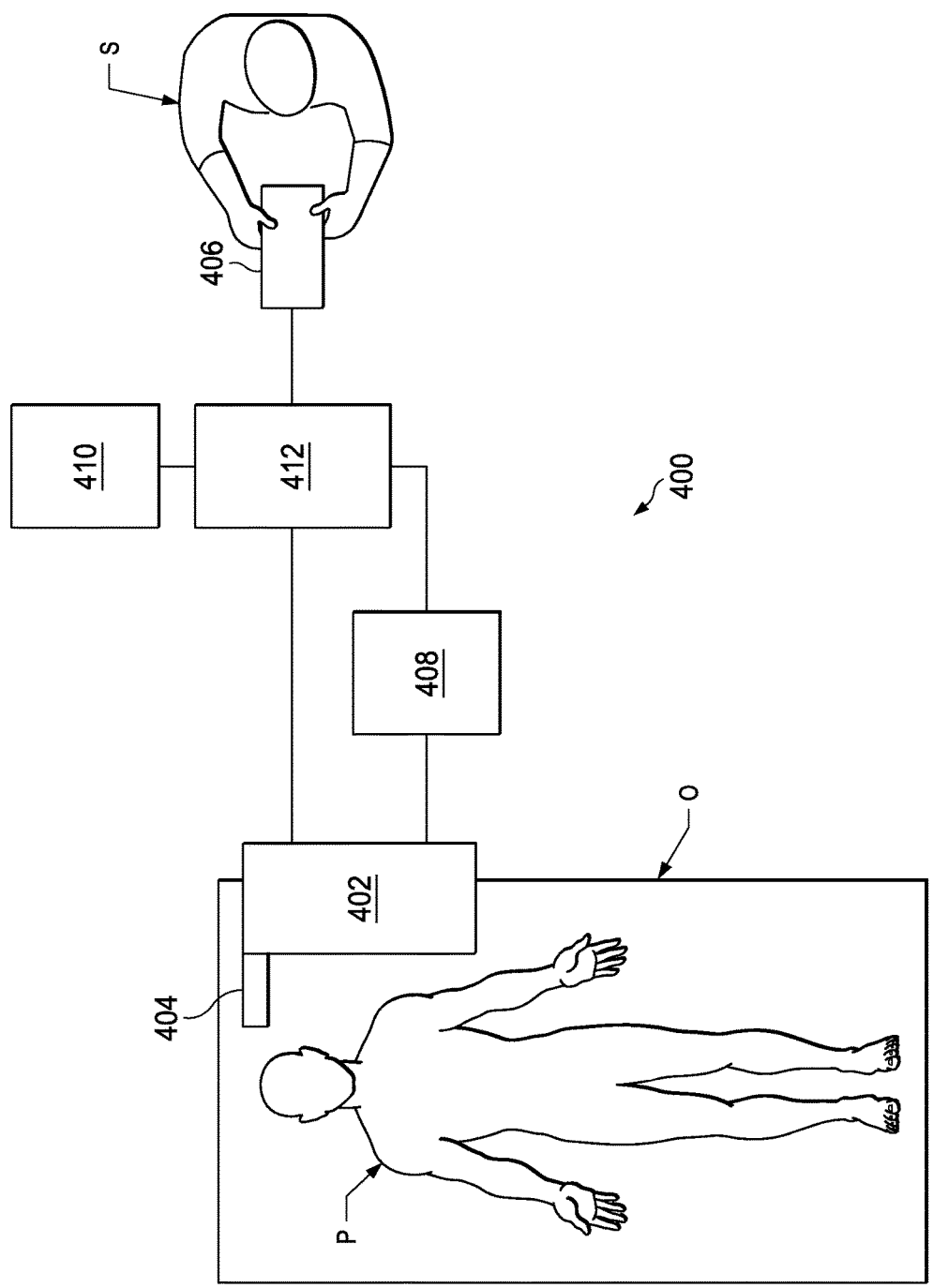
FIG. 16 is a robotic interventional system, in accordance with an embodiment of the present disclosure.

Any of the described sensor system configurations may be used to assist in medical interventional procedures, including computer assisted systems. Computer assisted systems may include teleoperated interventional systems such as robotic interventional systems. Referring to FIG. 16 of the drawings, a teleoperated interventional system for use in, for example, surgical, diagnostic, therapeutic, or biopsy procedures, is generally indicated by the reference numeral 400. As shown in FIG. 1, the teleoperated interventional system 400 generally includes a robotic assembly 402 mounted to or near an operating table O on which a patient P is positioned. An interventional instrument system 404 is operably coupled to the robotic assembly 402. An operator input system 406 allows a surgeon S to view the surgical site and to control the operation of the interventional instrument system 404.

The operator input system 406 may be located at a surgeon's console which is usually located in the same room as operating table O. However, it should be understood that the surgeon S can be located in a different room or a completely different building from the patient P. Operator input system 406 generally includes one or more control device(s) for controlling the interventional instrument system 404. The control device(s) may include any number of a variety of input devices, such as hand grips, joysticks, trackballs, data gloves, trigger-guns, hand-operated controllers, voice recognition devices, touch screens, body motion or presence sensors, or the like. In some embodiments, the control device(s) will be provided with the same degrees of freedom as the interventional instruments of the robotic assembly to provide the surgeon with telepresence, or the perception that the control device(s) are integral with the instruments so that the surgeon has a strong sense of directly controlling instruments. In other embodiments, the control device(s) may have more or fewer degrees of freedom than the associated interventional instruments and still provide the surgeon with telepresence. In some embodiments, the control device(s) are manual input devices which move with six degrees of freedom, and which may also include an actuatable handle for actuating instruments (for example, for closing grasping jaws, applying an electrical potential to an electrode, delivering a medicinal treatment, or the like).

The robotic assembly 402 supports the interventional instrument system 404 and may comprise a kinematic structure of one or more non-servo controlled links (e.g., one or more links that may be manually positioned and locked in place, generally referred to as a set-up structure) and a robotic manipulator. The robotic assembly 402 includes plurality of actuators (e.g., motors) that drive inputs on the interventional instrument 404. These motors actively move in response to commands from the control system (e.g., control system 412). The motors include drive systems which when coupled to the interventional instrument 404 may advance the interventional instrument into a naturally or surgically created anatomical orifice and/or may move the distal end of the interventional instrument in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the motors can be used to actuate an articulable end effector of the instrument for grasping tissue in the jaws of a biopsy device or the like.

The robotic interventional system 400 also includes a sensor system 408 with one or more sub-systems for receiving information about the instruments of the robotic assembly. The sensor system 408 may include, for example, the shape sensor device 10 in any of the configurations described above. The sensor sub-systems may also include an electromagnetic (EM) position sensor system and/or a visualization system for capturing images from the distal end of the instrument.

The robotic interventional system 400 also includes a display system 410 for displaying an image of the surgical site and interventional instruments 404 generated by sub-systems of the sensor system 408. The display 410 and the operator input system 406 may be oriented so the operator can control the interventional instrument system 404 and the operator input system 406 as if viewing the workspace in substantially true presence. True presence means that the displayed tissue image appears to an operator as if the operator was physically present at the image location and directly viewing the tissue from the perspective of the image.

Alternatively or additionally, display system 410 may present images of the surgical site recorded and/or modeled preoperatively using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, or the like. The presented preoperative images may include two-dimensional, three-dimensional, or four-dimensional (including e.g., time based or velocity based information) images and models.

In some embodiments, the display system 410 may display a virtual visualization image in which the actual location of the interventional instrument is registered (e.g., dynamically referenced) with preoperative or concurrent images to present the surgeon with a virtual image of the internal surgical site at the location of the tip of the surgical instrument.

In other embodiments, the display system 410 may display a virtual visualization image in which the actual location of the interventional instrument is registered with prior images (including preoperatively recorded images) or concurrent images to present the surgeon with a virtual image of an interventional instrument at the surgical site. An image of a portion of the interventional instrument 404 may be superimposed on the virtual image to assist the surgeon controlling the interventional instrument.

The robotic interventional system 400 also includes a control system 412. The control system 412 includes at least one processor (not shown), and typically a plurality of processors, for effecting control between the interventional instrument system 404, the operator input system 406, the sensor system 408, and the display system 410. The control system 412 may include common computer components including a logic unit, such as an arithmetic or logical adder, and one or more memory devices. The control system 412 also includes programmed instructions (e.g., a computer-readable medium storing the instructions) to implement some or all of the methods described herein.

While control system 412 is shown as a single block in the simplified schematic of FIG. 1, the system may comprise a number of data processing circuits with a portion of the processing optionally being performed on or adjacent the robotic assembly 402, a portion being performed at the operator input system 406, and the like. The control system 24 and the sensor processing and control system 27 may be components of the control system. Any of a wide variety of centralized or distributed data processing architectures may be employed. Similarly, the programmed instructions may be implemented as a number of separate programs or subroutines, or they may be integrated into a number of other aspects of the robotic systems described herein. In one embodiment, control system 412 supports wireless communication protocols such as Bluetooth, IrDA, HomeRF, IEEE 802.11, DECT, and Wireless Telemetry.

In some embodiments, control system 412 may include one or more servo controllers to provide force and torque feedback from the interventional instrument system 404 to one or more corresponding servomotors for the operator input system 406. The servo controller(s) may also transmit signals instructing robotic assembly 402 to move the interventional instruments 404 which extend into an internal surgical site within the patient body via openings in the body. Any suitable conventional or specialized servo controller may be used. A servo controller may be separate from, or integrated with, robotic assembly 402. In some embodiments, the servo controller and robotic assembly are provided as part of a robotic arm cart positioned adjacent to the patient's body.

The control system 412 may further include a virtual visualization system to provide navigation assistance to the interventional instruments 404. Virtual navigation using the virtual visualization system is based upon reference to an acquired dataset associated with the three dimensional structure of the anatomical passageways. More specifically, the virtual visualization system processes images of the surgical site recorded and/or modeled using imaging technology such as computerized tomography (CT), magnetic resonance imaging (MRI), fluoroscopy, thermography, ultrasound, optical coherence tomography (OCT), thermal imaging, impedance imaging, laser imaging, nanotube X-ray imaging, digitizing probe acquisitions or the like. Software is used to convert the recorded images into a two dimensional or three dimensional model of a partial or an entire anatomical organ or anatomical region. The model describes the various locations and shapes of the passageways and their connectivity. The images used to generate the model may be recorded preoperatively or intra-operatively during a clinical procedure. In an alternative embodiment, a virtual visualization system may use standard models (i.e., not patient specific) or hybrids of a standard model and patient specific data.

During a virtual navigation procedure, the sensor system 408 may be used to compute an approximate location of the instrument with respect to the patient anatomy. The location can be used to produce both macro-level tracking images of the patient anatomy and virtual internal images of the patient anatomy. Various systems for using fiber optic sensors to register and display an interventional implement together with preoperatively recorded surgical images, such as those from a virtual visualization system, are known. For example U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety, discloses one such system.

The robotic interventional system 400 may further include optional operation and support systems (not shown) such as illumination systems, steering control systems, irrigation systems, and/or suction systems. In alternative embodiments, the robotic system may include more than one robotic assembly and/or more than one operator input system. The exact number of manipulator assemblies will depend on the surgical procedure and the space constraints within the operating room, among other factors. The operator input systems may be collocated, or they may be positioned in separate locations. Multiple operator input systems allow more than one operator to control one or more manipulator assemblies in various combinations.

One or more elements in embodiments of the invention may be implemented in software to execute on a processor of a computer system such as control system 412. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device, The code segments may be downloaded via computer networks such as the Internet, intranet, etc.

Note that the processes and displays presented may not inherently be related to any particular computer or other apparatus. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method comprising:
receiving first shape data from a first elongated optical fiber section in a first shape sensor, the first elongated optical fiber section extending between a reference fixture and a first anatomic fixture coupled to a patient anatomy;
determining a pose of the first anatomic fixture relative to the reference fixture from the first shape data;
tracking a pose change for the first anatomic fixture based on the pose from the first shape data;
receiving second shape data from a second shape sensor extending between the reference fixture and an instrument fixture coupled to a medical instrument;
determining a first pose of the instrument fixture relative to the reference fixture from the second shape data;
tracking a first pose change of the first pose for the instrument fixture;
receiving third shape data from a second elongated optical fiber section of the first shape sensor extending between the first anatomic fixture and the instrument fixture;
determining a second pose of the instrument fixture relative to the reference fixture from the third shape data and the first shape data;
tracking a second pose change of the second pose for the instrument fixture; and
evaluating an instrument fixture pose redundancy based on the first pose and the second pose of the instrument fixture.

2. The method of claim 1 further comprising:
receiving fourth shape data from a third shape sensor including a third elongated optical fiber section extending between the reference fixture and the first anatomic fixture coupled to the patient anatomy;
determining a pose of the first anatomic fixture relative to the reference fixture from the fourth shape data; and
tracking a pose change for the first anatomic fixture based on the pose from the fourth shape data.

3. The method of claim 1 wherein the medical instrument is a probe adapted to digitize point locations.

4. The method of claim 1 wherein the second shape sensor extends within a cable including a power supply component or a communication component.

5. The method of claim 1 wherein determining a pose of the first anatomic fixture relative to the reference fixture from the first shape data includes integrating transformations for a plurality of discrete shape estimates from the first shape data.

6. The method of claim 1 wherein receiving the third shape data includes receiving fourth shape data from a third elongated optical fiber section extending between the first anatomic fixture and a second anatomic fixture coupled to the patient anatomy, wherein the second elongated optical fiber section includes the third elongated optical fiber section.

7. The method of claim 6 wherein receiving fourth shape data includes receiving the fourth shape data through the first elongated optical fiber section.

8. The method of claim 1 wherein the first shape sensor is coupled to a surgical drape.

9. The method of claim 8 wherein the first anatomic fixture is coupled to the surgical drape.

10. The method of claim 1 wherein the first anatomic fixture is a bone fixation device.

11. The method of claim 1 further comprising receiving instrument data signals on the first elongated optical fiber section, the instrument data signals including an instrument status, an instrument identification, a usage count, or applied force strain information.

12. The method of claim 1 wherein the first elongated optical fiber section is releasably couplable to the first anatomic fixture by a coupling mechanism.

13. The method of claim 1 wherein the first shape sensor includes a third elongated optical fiber section extending between the reference fixture and the first anatomic fixture and wherein the first and third elongated optical fiber sections are coupled to a support material and separated by a lateral distance in a spaced apart configuration by the support material, wherein the support material maintains the lateral distance between the first and third elongated optical fiber sections.

14. The method of claim 13 further comprising:
receiving fourth shape data from the third elongated optical fiber section of the first shape sensor; and
combining the first and fourth shape data to determine the pose of the first anatomic fixture relative to the reference fixture.

15. The method of claim 1 wherein the medical instrument includes a digitizing probe, a bone abrasion tool, a tissue cutting tool, an ablation instrument, a tissue approximation instrument, a biopsy instrument, an impedance measurement instrument, a tissue imaging instrument, or a therapeutic instrument.

16. A system comprising:
a reference fixture;
a first anatomic fixture configured to be coupled to a patient anatomy;
an instrument fixture coupled to a medical instrument;
a first shape sensor including:
a first elongated optical fiber section extending between the reference fixture and the first anatomic fixture; and
a second elongated optical fiber section extending between the first anatomic fixture and the instrument fixture;
a second shape sensor extending between the reference fixture and the instrument fixture; and
a processor configured for:
receiving first shape data from the first elongated optical fiber section of the first shape sensor;
determining a pose of the first anatomic fixture relative to the reference fixture from the first shape data;
tracking a pose change for the first anatomic fixture based on the pose from the first shape data;
receiving second shape data from the second shape sensor;
determining a first pose of the instrument fixture relative to the reference fixture from the second shape data;
tracking a first pose change of the first pose for the instrument fixture;
receiving third shape data from the second elongated optical fiber section of the first shape sensor;
determining a second pose of the instrument fixture relative to the reference fixture from the third shape data and the first shape data;
tracking a second pose change of the second pose for the instrument fixture; and
evaluating an instrument fixture pose redundancy based on the first pose and the second pose of the instrument fixture.

17. The system of claim 16 further comprising:
a third shape sensor including a third elongated optical fiber section extending between the reference fixture and the first anatomic fixture,
wherein the processor is further configured for:
receiving fourth shape data from the third shape sensor;
determining a pose of the first anatomic fixture relative to the reference fixture from the fourth shape data; and
tracking a pose change for the first anatomic fixture based on the pose from the fourth shape data.

18. The system of claim 16 further comprising:
a second anatomic fixture configured to be coupled to the patient anatomy, wherein:
the first shape sensor further includes:
a third elongated optical fiber section extending between the first anatomic fixture and the second anatomic fixture;
receiving the third shape data includes receiving fourth shape data from the third elongated optical fiber section; and
the second elongated optical fiber section includes the third elongated optical fiber section.

19. The system of claim 16 wherein:
the first shape sensor further includes a third elongated optical fiber section extending between the reference fixture and the first anatomic fixture;
the first and third elongated optical fiber sections are coupled to a support material and separated by a lateral distance in a spaced apart configuration by the support material, wherein the support material maintains the lateral distance between the first and third elongated optical fiber sections; and
the processor is further configured for:
receiving fourth shape data from the third elongated optical fiber section of the first shape sensor; and
combining the first and fourth shape data to determine the pose of the first anatomic fixture relative to the reference fixture.

20. The system of claim 16 wherein the medical instrument includes a digitizing probe, a bone abrasion tool, a tissue cutting tool, an ablation instrument, a tissue approximation instrument, a biopsy instrument, an impedance measurement instrument, a tissue imaging instrument, or a therapeutic instrument.

* * * * *